(12) United States Patent
Zaltieri et al.

(10) Patent No.: US 11,427,678 B2
(45) Date of Patent: Aug. 30, 2022

(54) MODIFIED POLYESTER HAVING ANTIBACTERIAL PROPERTIES AND USE OF THE MODIFIED POLYESTER

(71) Applicant: GOLDEN LADY COMPANY S.P.A., Castiglione delle Stiviere (IT)

(72) Inventors: Mauro Zaltieri, Castelnuovo di Asola (IT); Nerino Grassi, Castiglione delle Stiviere (IT); Maurizio Masi, Milan (IT); Filippo Rossi, Arezzo (IT)

(73) Assignee: GOLDEN LADY COMPANY S.P.A., Castiglione delle Stiviere (IT)

( * ) Notice: Subject to any disclaimer, the term of this patent is extended or adjusted under 35 U.S.C. 154(b) by 206 days.

(21) Appl. No.: 16/487,213

(22) PCT Filed: Feb. 6, 2018

(86) PCT No.: PCT/IB2018/050726
§ 371 (c)(1),
(2) Date: Aug. 20, 2019

(87) PCT Pub. No.: WO2018/154403
PCT Pub. Date: Aug. 30, 2018

(65) Prior Publication Data
US 2021/0139646 A1  May 13, 2021

(30) Foreign Application Priority Data
Feb. 21, 2017  (IT) .................. 102017000019556

(51) Int. Cl.
| | | |
|---|---|---|
| C08G 63/91 | (2006.01) |
| A01N 37/30 | (2006.01) |
| A61L 15/26 | (2006.01) |
| A61L 15/44 | (2006.01) |
| D01F 6/62 | (2006.01) |
| A61L 29/16 | (2006.01) |
| A61L 29/06 | (2006.01) |
| A61L 27/18 | (2006.01) |
| A61L 27/54 | (2006.01) |
| D01F 6/86 | (2006.01) |

(52) U.S. Cl.
CPC .......... *C08G 63/916* (2013.01); *A01N 37/30* (2013.01); *A61L 15/26* (2013.01); *A61L 15/44* (2013.01); *A61L 27/18* (2013.01); *A61L 27/54* (2013.01); *A61L 29/06* (2013.01); *A61L 29/16* (2013.01); *D01F 6/62* (2013.01); *D01F 6/86* (2013.01); *A61L 2300/404* (2013.01); *D10B 2401/13* (2013.01)

(58) Field of Classification Search
CPC . A61L 2400/12; A61L 2300/404; A61K 9/70; D01F 6/86
See application file for complete search history.

(56) References Cited

U.S. PATENT DOCUMENTS

| 4,503,197 A | 3/1985 | Speranza et al. |
| 5,986,041 A | 11/1999 | Cheng et al. |

FOREIGN PATENT DOCUMENTS

| CN | 101173041 A | 5/2008 |
| CN | 101495564 A | 7/2009 |
| CN | 103 881 335 A | 6/2014 |
| CN | 105200550 A | 12/2015 |
| JP | H1121346 A | 1/1999 |
| JP | 2010126814 A | 6/2010 |
| WO | 93/25587 A1 | 12/1993 |
| WO | 99/47579 A1 | 9/1999 |
| WO | 2008011940 A1 | 1/2008 |
| WO | 2014/057364 A1 | 4/2014 |
| WO | 2015/001515 A1 | 1/2015 |

OTHER PUBLICATIONS

Jeffamine ED-2011, 8 pages, Mar. 20, 2020.*
Madson R.E. Santos et al., "Recent Developments in Antimicrobial Polymers: A review", in Materials, 2016, 9, 599; doi:10.3390/ma9070599 (www.mdpi.com/journal/materials).
Xan Xue et al., "Antimicrobial Polymeric Materials with Quaternary Ammonium and Phosphonium Salts", in International Journal of Molecular Sciences, 2015, 16, 3626-3655; doi: 10.3390/ijms16023626 (www.mdpi.com/journals/ijms).
Diana Santos Morais et al. "Antimicrobial Approaches for Textiles: From Research to Market", in Materials, 2016, 9, 498; doi:10.3390/ma9060498, (www.mdpi.com/journal/materials).
Felix Siedenbiedel et al., "Antimicrobial Polymers in Solution and Surfaces: Overview and Functional Principles", in Polymers 2012, 4, 46-71; doi:10.3390/ polym4010046 (www.mdpi.com/journal/polymers).
Sheila Shahidi et al., "Antibacterial Agents in Textile Industry", in "Antimicrobial Agents", published by Varaprasad Bobbarala, ISBN 978-953-51-0723-1, Sep. 12, 2012, chapter 19, pp. 388-406.
A. Pinon et al., "Microbiological Contamination of Bed Linen and Staff Uniforms in a Hospital", in Advances in Microbiology, 2013, 3, 515-519, published online on http://www.scirp.org/journal/aim and http://dx.doi.org/l0.4236/aim.2013.37069.
S. Fijan et al., "Hospital Textiles, Are They a Possible Vehicle for Healthcare-Associated Infections?", in Int. J. Environ. Res. Public Health 2012, 9, 3330-3343; doi: 10.3390/ijerph9093330, published in www.mdpi.com/journal/jerph.
V.P. Shastri, "Non-Degradable Biocompatible Polymers in Medicine: Past, Present and Future", in Current Pharmaceutical Biotechnology, 2003, 4, 331-337.
W. Khan et al. "Implantable Medical Devices", in Focal Controlled Drug Delivery, chap.2, by A.J. Domb and W. Khan; Advances in Delivery Science and Technology, DOI 10.1007/978-1-4614-9434-8_2, available on http://www.springer.com/gp/book/9781461494331.
L.W. McKeen, "Plastics Used in Medical Devices", in Handbook of Polymer Applications in Medicine and Medical Devices. DOI: http://dx.doi.org/10.1016/B978-0-323-22805-3.00003.7, 2014 published by Elsevier Inc. (https://www.elsevier.com/_data/assets/pdf_file/0011/91649/Plastics-Used-in-Medical-Devices_link.pdf).

(Continued)

*Primary Examiner* — Kyle A Purdy
(74) *Attorney, Agent, or Firm* — McGlew and Tuttle, P.C.

(57) ABSTRACT

A polyethylene terephthalate functionalized with polyether amine to obtain antibacte-rial properties is described. Described are also uses of and methods for producing this functionalized polyester.

8 Claims, 1 Drawing Sheet

(56) References Cited

OTHER PUBLICATIONS

M.P. Maitz, "Applications of Synthetic Polymers in Clinical Medicine", in Biosurface and Biotribology.

* cited by examiner

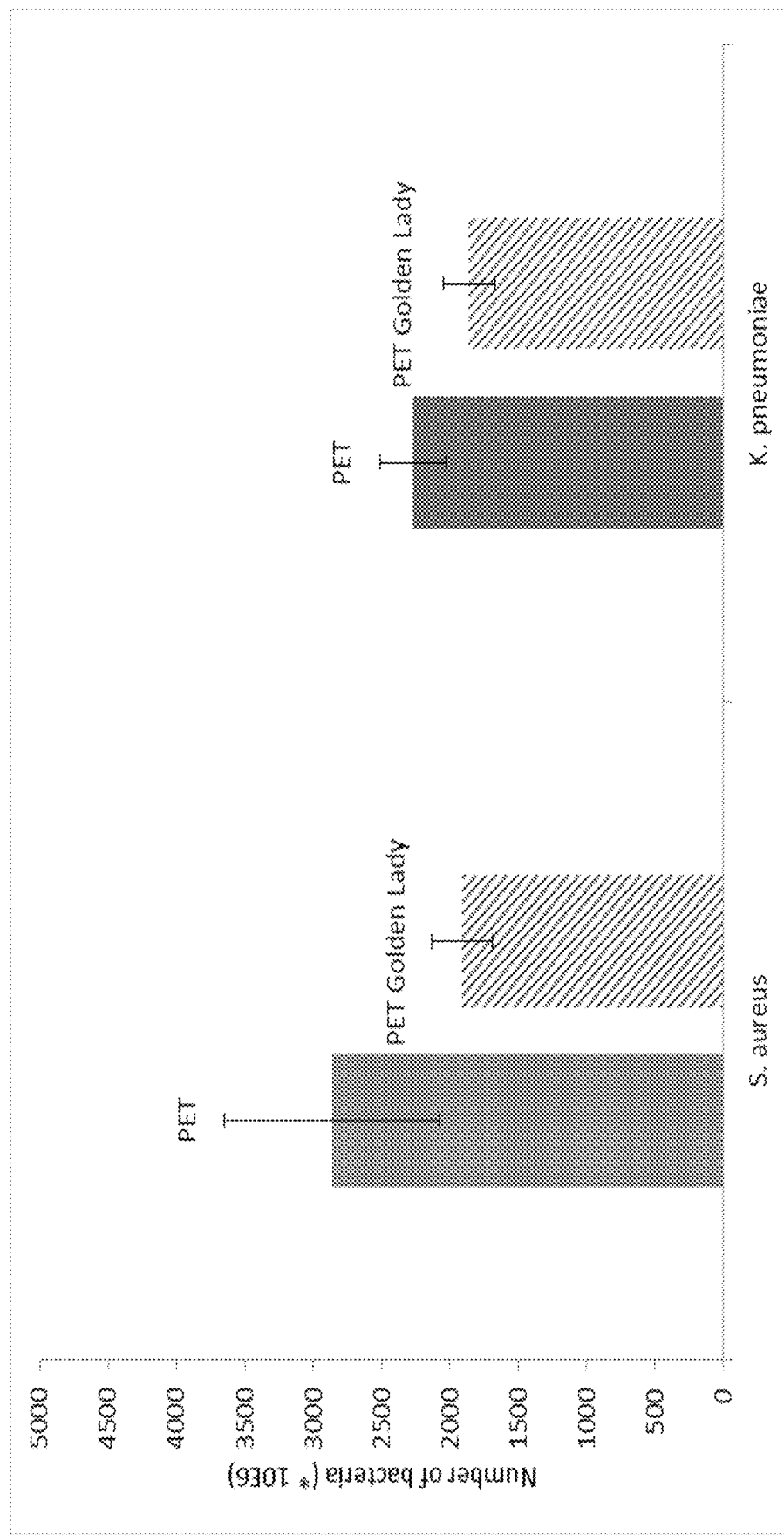

MODIFIED POLYESTER HAVING ANTIBACTERIAL PROPERTIES AND USE OF THE MODIFIED POLYESTER

TECHNICAL FIELD

The present invention relates to the field of polymers. In particular, aspects disclosed herein relate to improvements to polymers for producing synthetic threads, fibers and yarns, for example for producing woven, nonwoven or other textile articles. Further aspects relate to improvements to polymers for producing articles for medical use.

Embodiments disclosed herein relate to improvements to polyesters and in particular to polyethylene terephthalate (hereinafter also PET) and new uses of these polymers.

BACKGROUND ART

In the production of textile articles, for example for the apparel, furnishing, automotive field, and also for the medical and healthcare field, an increasing need exists to confer antimicrobial or antibacterial properties on threads, yarns or fibers used to produce articles of manufacture, and on articles obtained with these semi-finished products. The need to confer antibacterial or bacteriostatic properties on semi-finished products for manufacturing textile articles is on the one hand linked to health and hygiene and on the other to non-pathological collateral effects, linked to the presence and to the growth of microorganisms in textile articles destined for apparel or in any case for uses that require contact with the skin. Health and hygiene reasons relate to the need to reduce the transmission of pathogens through textile articles, for example in industrial or hospital environments. Collateral effects relating to the presence and to the growth of microorganisms, especially on apparel, are to be recognized in particular in that microorganisms are responsible for producing bad smell.

Many studies have been conducted aimed at producing polymers, in particular for manufacturing textile articles made of synthetic fibers or threads, with biocidal capacities. In general, the methods for conferring antibacterial or bacteriostatic capacities on polymers are divided into three macro-categories:

- biocidal polymers: these are polymers that have intrinsic antibacterial activity, usually based on the use of polycations, which are adapted to kill microorganisms through action on their cell membrane;
- polymeric biocides: these are polymers with no intrinsic antibacterial activity, to which biocide molecules are functionally connected. Usually, polymeric biocides are less effective than biocidal polymers, due to the steric impediment that characterizes them. As known, steric impediment is defined as the effect that the spatial distribution of atoms in the structure of a molecule can have in delaying or preventing a chemical reaction. The molecules with biocidal characteristics used in these cases are complex, relatively unstable to temperatures, costly and in general difficult to treat;
- biocide-releasing polymers: these are polymers without antibacterial capacity of their own, to which biocide molecules, which are released over time, have been attached. In substance, these are polymeric matrices loaded with biocide molecules entrapped with different methods in the matrix. These polymers have many disadvantages, on the one hand in that the released biocides are pollutants, and on the other in that the biocide load of the polymer runs out over time and has to be reloaded.

A wide overview on the recent developments of antibacterial polymers can be found in: Madson R. E. Santos et al., "*Recent Developments in Antimicrobial Polymers: A review*", in Materials, 2016, 9, 599; doi:10.3390/ma9070599 (www.mdpi.com/journal/materials); Xan Xue et al., "*Antimicrobial Polymeric Materials with Quaternary Ammonium and Phosphonium Salts*", in International Journal of Molecular Sciences, 2015, 16, 3626-3655; doi: 10.3390/ijms16023626 (www.mdpi.com/journals/ijms); Diana Santos Morals et al. "*Antimicrobial Approaches for Textiles: From Research to Market*", in Materials, 2016, 9, 498; doi:10.3390/ma9060498, (www.mdpi.com/journal/materials); Felix Siedenbiedel et al, "*Antimicrobial Polymers in Solution and Surfaces: Overview and Functional Principles*", in Polymers 2012, 4, 46-71; doi:10.3390/polym4010046 (www.mdpi.com/journal/polymers); Sheila Shahidi et al, "*Antibacterial Agents in Textile Industry*", in "*Antimicrobial Agents*", published by Varaprasad Bobbarala, ISBN 978-953-51-0723-1, Sep. 12, 2012, chapter 19, pages 388-406.

The need to use textile articles with antibacterial properties in the medical and hospital field arises from the fact that these articles can become dangerous vehicles for spreading microorganisms. Risks deriving from bacterial contaminations of textile articles used in the medical and hospital field are also discussed in A. Pinon et al., "*Microbiological Contamination of Bed Linen and Staff Uniforms in a Hospital*", in Advances in Microbiology, 2013, 3, 515-519, published online on http://www.scirp.org/journal/aim; http://dx.doi.org/10.4236/aim.2013.37069 and in S. Fijan et al., "*Hospital Textiles, Are They a Possible Vehicle for Healthcare-Associated Infections?*", in Int. J. Environ. Res. Public Health 2012, 9, 3330-3343; doi:10.3390/ijerph9093330, published in www.mdpi.com/journal/ijerph.

As mentioned in the above-mentioned technical and scientific literature, considerable technical difficulties and/or drawbacks are encountered in the production of polymers with antibacterial properties during converting into fiber, or during use of the semi-finished product and of the fabric obtainable from said semi-finished product. Moreover, the above-mentioned literature shows that there is an increasing need for polymers with biocidal properties, especially in the apparel field and in the medical field.

Therefore, there is continual research for solutions that are more financially advantageous, more effective and less polluting for producing textile articles with antibacterial properties.

In addition to uses for producing of textile fibers and threads, and related articles manufactured therewith, polymeric materials have many other applications in the medical field, in which antibacterial properties would be useful. For an overview on the uses of polymeric materials in medicine and surgery see V. P. Shastri, "*Non-Degradable Biocompatible Polymers in Medicine: Past, Present and Future*", in Current Pharmaceutical Biotechnology, 2003, 4, 331-337; W. Khan et al. "*Implantable Medical Devices*", in *Focal Controlled Drug Delivery*, chap. 2, by A. J. Domb and W. Khan; Advances in Delivery Science and Technology, DOI 10.1007/978-1-4614-9434-8_2, available on http://www.springer.com/gp/book/9781461494331; L. W. McKeen, "*Plastics Used in Medical Devices*", in "*Handbook of Polymer Applications in Medicine and Medical Devices*. DOI: http://dx.doi.org/10.1016/B978-0-323-22805-3.00003.7, 2014 published by Elsevier Inc. (https:// www.elsevier.com/_data/assets/pdf_file/0011/91649/Plastics-Used-in-Medical-Devices_link.pdf); M. F. Maltz, "*Applications of Synthetic Polymers in Clinical Medicine*", in Biosurface and Biotribology 1 (2015) 161-176, available online at www.sciencedirect.com.

It would be beneficial to have polymers with antibacterial properties for use in the medical and surgical field.

SUMMARY

It has surprisingly been discovered that antibacterial property can be conferred on a polyester by modifying the polyethylene terephthalate chain with the introduction of at least a polyether amine. The modified polyester obtained through functionalization with polyether amine has exhibited biocidal capacities, i.e. the ability to reduce, with respect to an equivalent polyethylene terephthalate without polyether amine, the growth of bacterial colonies inoculated on polymer samples.

Therefore, according to one aspect, the present invention relates to a polyester containing polyethylene terephthalate and at least a polyether amine, in particular as a polymer having improved antibacterial capacities. The modified polyester is therefore a functionalized polyester containing a polyethylene terephthalate chain containing moieties of one or more polyether amines.

While in the embodiments illustrated herein a single polyether amine is used in combination with polyethylene terephthalate, to functionalize this latter by introducing moieties of the polyether amine into its chain, it would also be possible to use several polyether amines in combination, for example also with a variable number of amino groups (for example polyether diamines, polyether monoamines and polyether triamines).

Within the scope of the present disclosure and of the appended claims, unless otherwise specified, antibacterial capacities or antibacterial properties is meant generically as the capacity to reduce or prevent the growth of microorganisms, in particular bacteria, microbes, fungi and viruses. Therefore, the antibacterial capacity can also comprise an antifungal or antimycotic capacity.

The use of polyether amines as molecules for the functionalization of polymers is known. WO2014/057364 and WO2015/001515 describe methods for producing modified polyamides, comprising nylon and a polyether diamine, to increase moisture regain, i.e. the capacity to absorb and retain moisture. In particular, these modified polyamides are suggested to improve the feel of fabrics and garments obtained therewith. However, these documents relate to a different family of polymers and suggest the use of polyether amines for other purposes.

The introduction of at least a polyether amine into the polyethylene terephthalate chain increases the antibacterial properties of the polyester, i.e. makes it possible to obtain a modified polyester that, when compared with the same polyester without polyether amine, has greater antibacterial capacity. The polyether amine and the polyethylene terephthalate are bonded to each other with covalent bonds in the polymer chain of the polyester. In this way, the antibacterial properties conferred by the polyether amine are stable and lasting, even if the polyester is subjected to chemical, thermal or mechanical actions, such as extrusion, washing, sterilization processes or the like, for example to produce threads, filaments, fibers or other semi-finished products, to wash or sterilize textile articles such as fabrics, nonwovens or the like, obtained from threads or fibers of modified polyester.

The mechanisms through which the surprising effect, on which the various aspects described herein are based, is obtained are not entirely clear. It is presumed, but this must not be understood as a limitation to the scope of the invention, that amino groups present in the polyether amine obstruct the growth of microorganisms, conferring biostatic properties on the modified polyethylene terephthalate.

Preferably, the polyether amine is prevalently positioned as chain terminal in the polyethylene terephthalate, with a free amino terminal ($NH_2$).

The polyether amine can be a polyether monoamine.

In currently preferred embodiments, the polyether amine comprises more than one amino group and can therefore be a polyether diamine or a polyether triamine, for instance.

The polyether amine can be present in a percentage by weight equal to at least about 1%, preferably equal to at least about 2%, more preferably equal to at least about 5%, with respect to the total weight of the polyester. In embodiments described herein the polyether amine can be present in an amount by weight no greater than about 50%, preferably no greater than about 30%, more preferably no greater than about 25%, even more preferably no greater than about 20%, with respect to the total weight of the polyester. For example, the percentage by weight of polyether amine in the polyester can be comprised between about 1% and about 50%, preferably between about 1% and about 25%. In some embodiments the polyester comprises a percentage of polyether amine comprised between about 1% and about 20%, for example between about 2% and about 20%, or between about 2.5% and about 15%.

In some embodiments, the polyester can comprise a percentage of polyethylene terephthalate of at least about 50% by weight, preferably at least about 60% by weight, more preferably at least about 70% by weight, even more preferably at least about 80% by weight, with respect to the total weight of the polyester. In embodiments described herein, the percentage by weight of polyethylene terephthalate is no greater than about 99%, preferably no greater than about 98% by weight, even more preferably no greater than about 95% by weight, with respect to the total weight of the polyester. For example, the polyester can comprise from about 50% to about 99% by weight, preferably between about 75% and about 99% by weight, for example between about 80% and about 99% by weight, or between about 80% and about 98%, or between about 85% and about 97.5% by weight of polyethylene terephthalate.

In some embodiments, the polyether amine has a weighted average molecular weight (Mw) equal to at least about 500 g/mol, preferably equal to at least about 800 g/mol, more preferably equal to at least 1000 g/mol, even more preferably equal to at least about 1500 g/mol, and preferably no greater than about 5000 g/mol, more preferably no greater than about 3000 g/mol, for example comprised between 1500 and 2800 g/mol.

The polyether amine-modified polyester disclosed herein can be used with particular advantage for the manufacture of textile products. In the present context, textile products are meant both as semi-finished products and as finished products. Semi-finished products can be meant as continuous monofilament or multifilament threads, staple fibers, or yarns obtained by spinning staple fibers. Semi-finished products can also be meant as cloths, tapes or tubular woven fabrics, or knitted fabrics, plies of nonwoven fabrics composed of bonded or unbonded fibers, threads or filaments, for example bonded mechanically, thermally, chemically, hydraulically, or in any other way, for example by a combination of two or more of the aforesaid bonding techniques.

Semi-finished products or textile articles can also consist of multi-ply products, for example formed of two or more joined plies of textile fibers or threads.

The textile product can comprise only polyester containing polyethylene terephthalate and at least a polyether amine, as described above. In some embodiments, the textile product can contain one or more further components in addition to the polyester containing PET and polyether amine. In some exemplary embodiments, different polymers can be combined with the polyester containing PET and polyether amine. For example, embodiments of the subject matter described herein can comprise bi-component threads or fibers, where one of the components consists of polyester containing PET and polyether amine, and the other component can consist of a different polymer, for example a polyamide, or polyethylene terephthalate without polyether amine.

The bi-component fibers or filaments can, for example, comprise a percentage by weight of polyester, containing polyethylene terephthalate and polyether amine, in a percentage equal to at least about 40% by weight, preferably equal to at least about 50% by weight, even more preferably equal to at least about 60% by weight of the total weight of the textile product.

Threads, filaments, fibers or yarns produced with modified polyester, containing polyethylene terephthalate and polyether amine as described herein, can be used as is or in a blend with other natural, artificial or synthetic threads, filaments, fibers or yarns, for example produced with other polymers such as polyester without polyether amine, or polyamide or other suitable components. In this case, in the textile product the polyester containing polyethylene terephthalate and polyether amine can be present in a percentage by weight equal to at least about 10%, preferably equal to at least about 50%, more preferably equal to at about 60% or 70%. Preferably, this percentage is no greater than about 95%, more preferably no greater than about 80% of the total weight of the textile product.

According to a further aspect, disclosed herein is a use of polyester containing polyethylene terephthalate and at least a polyether amine, for producing a product or article with antibacterial properties.

In particular, disclosed herein is the use of polyester containing polyethylene terephthalate and at least a polyether amine for producing a textile article with antibacterial properties. The textile article can be chosen in the group comprising: a nonwoven fabric consisting of bonded or unbonded fibers; a woven fabric; a knitted fabric; or combinations thereof.

According to a further aspect, disclosed herein is a method for conferring antibacterial properties on polyester containing polyethylene terephthalate, the method comprising the step of introducing a polyether amine into the chain of the polyethylene terephthalate, for example in a polymerization process, or subsequently to a polymerization process, causing already polymerized polyester and polyether amine to react.

According to a further aspect, disclosed herein is a method for producing polyester, in particular modified polyester with antibacterial properties, comprising reacting terephthalic acid, ethylene glycol and a polyether amine at temperatures and pressures sufficient to cause polymerization and formation of polyester containing polyethylene terephthalate and polyether amine.

In some embodiments, the method comprises the steps of:
reacting terephthalic acid and ethylene glycol with excess of ethylene glycol to obtain polyethylene terephthalate with terminal carboxyl groups;
reacting the terminal carboxyl groups with polyether amine and obtaining polyester containing a chain of polyethylene terephthalate and polyether amine.

According to other embodiments, the method provides for modifying already polymerized polyester, in order to introduce at least a polyether amine into the polyethylene terephthalate chain. The method can comprise the step of reacting polyethylene terephthalate with a polyether amine and obtaining a polyester having antibacterial properties and containing polyethylene terephthalate and polyether amine. The method can, for example, be implemented in an extruder for producing a continuous monofilament or multifilament thread, made of modified polyethylene terephthalate with polyether amine, having improved antibacterial capacities, starting from polyester containing polyethylene terephthalate for example in the form of chips, granules or the like, to which there is added, directly in the extruder or in a container separated from the extruder and for example in fluid connection therewith, a suitable amount of at least a polyether amine. The polyester reacts with the polyether amine and the thus modified polyester is extruded to form a semi-finished article, for example a thread, for textile applications or the like.

In other embodiments, the modified polyester thus obtained can be reconverted into a semi-finished product in the form of chips, granules or the like, for subsequent converting operations. In other words, when the functionalization reaction of the polyester with the polyether amine takes place starting from the already polymerized polyester, instead of from the starting monomers, the modified polyester can be used to produce a semi-finished product in any physical form, which can be intended for subsequent processes, including further melting and extrusion steps. The stability of the covalent chemical bond between the polyether amine and the polyethylene terephthalate ensures that the antibacterial properties obtained by introducing the polyether amine into the polyethylene terephthalate chain are maintained, even when the polymer is subjected to subsequent thermal cycles and mechanical processing operations.

To facilitate the reaction between already polymerized polyethylene terephthalate and polyether amine, in some embodiments the method can comprise the step of adding a grafter or a chain extender. The method can comprise the steps of reacting the grafter or the chain extender with the polyethylene terephthalate for obtaining a functionalized polyethylene terephthalate; and of reacting the functionalized polyethylene terephthalate with polyether amine.

According to a further aspect, the invention relates to the use of a polyester fiber or thread, containing polyethylene terephthalate and at least a polyether amine, for producing a textile article with antibacterial properties, for example a garment, a sheet, a blanket, a curtain, a gauze or a medical or surgical device.

The antibacterial properties obtained modifying the polyethylene terephthalate with the polyether amine make the polyester thus modified particularly suitable in all the applications in which an antibacterial property is desirable or beneficial, for instance in the medical-surgical field, but also in the apparel sector, where decrease of bacterial load reduces the production of bad smell deriving from perspiration.

Also disclosed herein is a method for producing a textile article comprising the step of converting a semi-finished product in the form of textile fiber or thread into a textile structure, such as a nonwoven fabric, a woven fabric, or a knitted fabric, comprising one or more plies, in which the semi-finished product comprises polyethylene terephthalate and a polyether amine, to increase the antibacterial properties of the textile structure.

In some embodiments, the polyether amine has at least two amino groups ($NH_2$), one of which is used to react with the polyethylene terephthalate and forms a covalent bond with the chain of the polyester, and the other remains available in the resulting polymer chain.

Features and embodiments are disclosed here below and are further set forth in the appended claims, which form an integral part of the present description. The above brief description sets forth features of the various embodiments of the present invention in order that the detailed description that follows may be better understood and in order that the present contributions to the art may be better appreciated. There are, of course, other features of the invention that will be described hereinafter and which will be set forth in the appended claims. In this respect, before explaining several embodiments of the invention in details, it is understood that the various embodiments of the invention are not limited in their application to the details of the construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which the disclosure is based, may readily be utilized as a basis for designing other structures, methods, and/or systems for carrying out the several purposes of the present invention. It is important, therefore, that the claims be regarded as including such equivalent constructions insofar as they do not depart from the spirit and scope of the present invention.

The use of modified polyester with polyether amines as described herein allows antibacterial properties to be obtained in textile threads and fibers, or other semi-finished or finished products, by means of a process that is easily implementable on an industrial scale. As a matter of fact, in particular, the process conditions for introducing the polyether amine into the polyethylene terephthalate chain have not changed greatly with respect to those used to produce a normal conventional polyethylene terephthalate, i.e. without polyether amine. Moreover, this approach has the undoubted advantage of being less costly with respect to other currently known industrial processes, aimed at obtaining similar effects in terms of increasing antibacterial properties.

BRIEF DESCRIPTION OF THE DRAWINGS

The invention will now be described with reference to a series of exemplary of embodiments and of results achievable therewith, illustrated in the accompanying drawings, in which FIG. 1 shows the antibacterial capacity of a fabric obtained using conventional PET threads and threads made of PET containing polyether diamine, i.e. functionalized with a polyether amine, according to the present disclosure.

DETAILED DESCRIPTION OF EMBODIMENTS

The following detailed description of embodiments given by way of example refers to the accompanying drawings.

The same reference numbers in different drawings identify identical or similar elements. Moreover, the drawings are not necessarily to scale. The following detailed description does not limit the invention. Rather, the scope of the invention is defined by the accompanying claims.

Reference in the description to "an embodiment" or "the embodiment" or "some embodiments" means that a particular characteristic, structure or element described in relation to an embodiment is included in at least one embodiment of the object described. Therefore, the phrase "in an embodiment" or "in the embodiment" or "in some embodiments" at various points of the description does not necessarily refer to the same embodiment(s). Furthermore, the particular features, structures or elements may be combined in any appropriate manner in one or more embodiments.

Ratios, concentrations, amounts and other numerical data illustrated and mentioned in the present description and in the appended claims can be expressed in the form of ranges. It must be understood that this form of expression is used for convenience and brevity. It must not be understood in the sense that a range comprises only the numerical data explicitly indicated as limits of the range. Instead, a range of values must be understood as extensive and flexible, in the sense of comprising all the numerical values individually contained in the range, and all the sub-ranges, delimited by any two numerical values contained in the range. Therefore, in general, the expression "a range from about A to about B" discloses not only the range defined by the ends A and B, but also any sub-range from "about X to about Y", where X and Y are values between A and B.

When a content of a substance A in a set B of substances is defined with a series of percentages of maximum values and a series of percentages of minimum values, it must be understood that the substance A can be contained in the set B with amount within a plurality of ranges each defined by a pair of any one of the minimum values and any one of the maximum values. For example, the definition "containing at least x %, preferably at least (x−n) %, and no more than y %, preferably no more than (y−m) %", comprises the ranges [x; y], [x; (y−m)], [(x−n); y], [(x−n); (y−m)]. Each of these ranges also comprises each sub-range defined between its maximum and minimum limits.

The term "about" can comprise rounding off to significant figures of numerical values.

The term "about" as used herein when referring to a numerical value or range of numerical values allows a degree of variability of the numerical value or of the range for example within 10%, or within 5% of the numerical value indicated or of the limit indicated of a range.

According to embodiments described herein, to obtain a polyester-based polymer, containing polyethylene terephthalate (PET) having an improved antibacterial capacity, polyether amine bonded to one or more monomers of polyethylene terephthalate in the polyester chain is used.

The polyester containing polyethylene terephthalate and polyether amine can be obtained starting from monomers (terephthalic acid and ethylene glycol) for producing polyethylene terephthalate, with batch or continuous polymerization reaction, during which at least a polyether amine is added.

Examples of polyether amines, and in particular of polyether diamines and polyether triamines that can be used in the methods and in the products described herein will be indicated below.

In some embodiments, the method provides for reacting terephthalic acid and ethylene glycol with an excess of ethylene glycol to obtain polyethylene terephthalate with terminal carboxyl groups, according to the reaction:

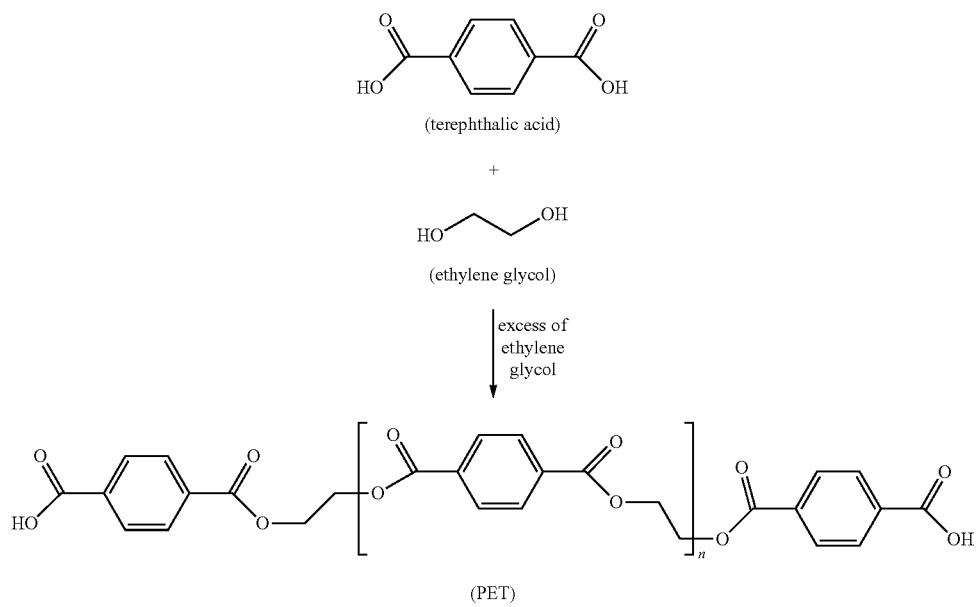

The reaction is conducted at pressures comprised between about 150° C. and about 200° C. and at pressure of about 4 bar with acid catalyst. The PET thus obtained is reacted with a polyether diamine obtaining modified polyethylene terephthalate with terminal groups $NH_2$, according to the reaction

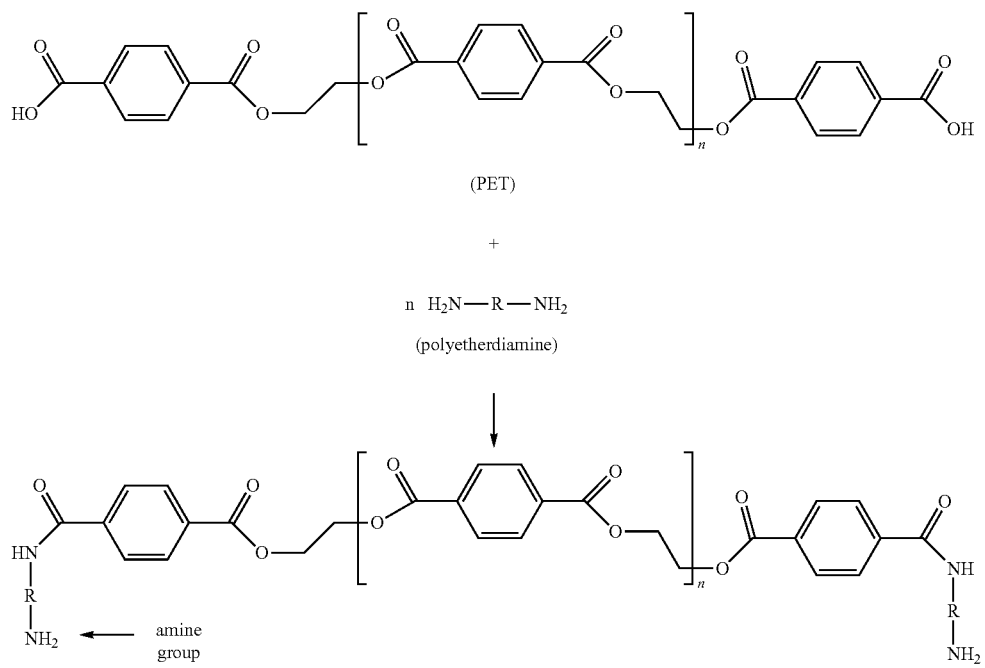

where $H_2N—R—NH_2$ is a generic polyether diamine, examples of which are given later on in the present description. The reaction can take place at temperatures comprised between about 120° C. and about 140° C. for 24 hours at atmospheric pressure.

The modified polyethylene terephthalate thus obtained can be in granules, chips or other suitable form and can be used in subsequent production processes, for example for molding, injection, co-molding, extrusion, blowing, etc.

In particular, the polyester containing polyethylene terephthalate and polyether amine thus obtained can be melted and extruded to obtain monofilament or multifilament threads, as semi-finished products for the subsequent production of textile articles. The continuous filaments can be cut into fibers, which can then be used for producing nonwoven fabrics, or can be spun to obtain continuous yarns.

In other embodiments, the modified polyester can be produced starting from already polymerized polyethylene terephthalate, for example in the form of chips, granules or the like, causing a functionalization reaction, through which molecules of polyether amine react with terminal groups of the molecules of polyethylene terephthalate, or with two consecutive monomers of the molecules of PET. The following reaction can take place between a chain terminal group of the polyethylene terephthalate and a generic polyether diamine H₂N—R—NH₂ obtaining the modified polyester with formation of ethanol:

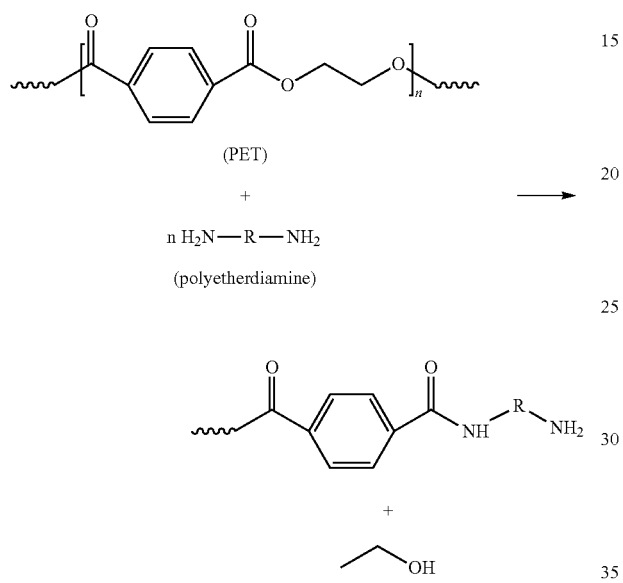

When the polyether amine molecule reacts with two monomers of polyethylene terephthalate inside the chain, vice versa, the following reaction will be obtained:

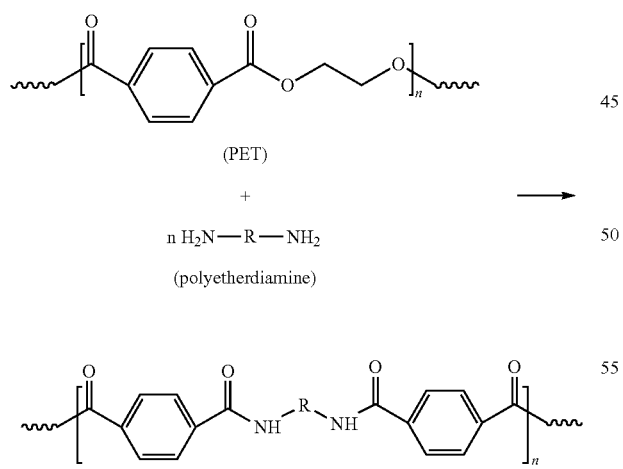

To facilitate the formation of polymer chains containing modified polyethylene terephthalate with the addition of polyether amine molecules starting from already polymerized polyethylene terephthalate, chain extenders or grafters can be used to facilitate the formation of bonds between the polyether amine molecule and the monomers of the polyethylene terephthalate. In some embodiments, a sequence of formaldehyde and bromoacetic acid can be used as chain extender. In a first step the previously polymerized polyethylene terephthalate reacts with the chain extender to form a polyethylene terephthalate functionalized with carboxyl group, according to the reactions

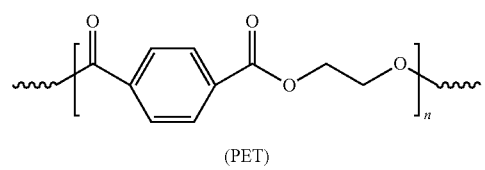
(PET)

+

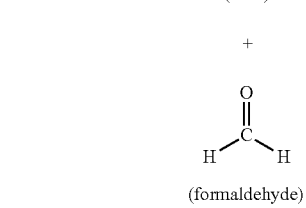
(formaldehyde)

↓

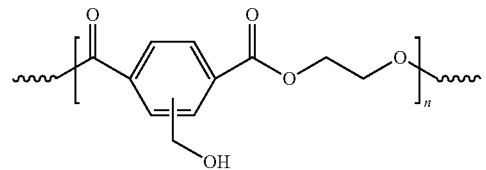

+

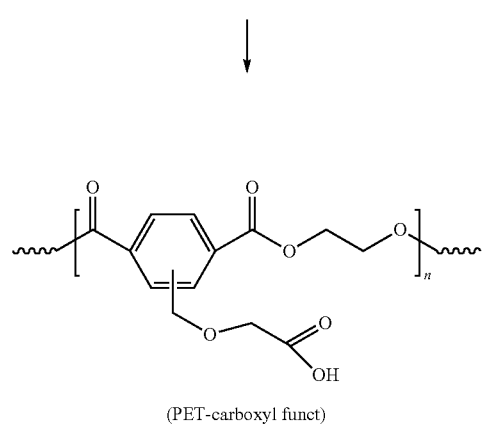
(PET-carboxyl funct)

The first reaction can be conducted at about 30° C. for about 4 hours in acetic acid 1M, while the second at about 30° C. in sodium hydroxide 2M for 18 h.

The molecules thus obtained can react with the respective terminal groups COOH through an amidation reaction with the polyether amine resulting in the polyester containing polyether amine according to the following reaction:

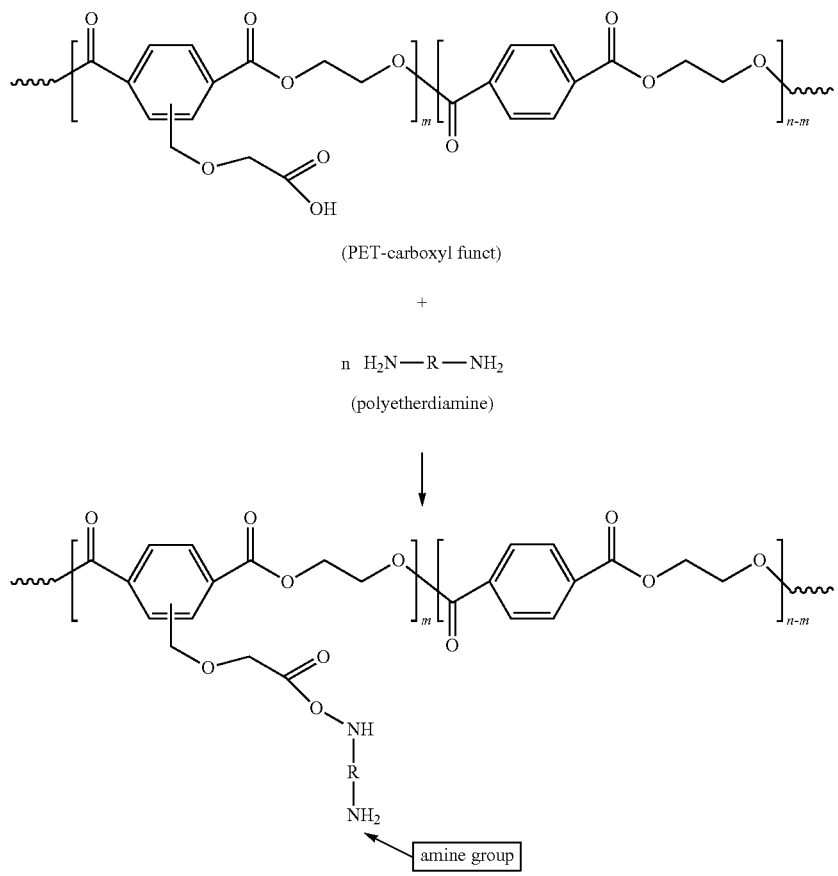

where H₂N—R—NH₂ once again represents a generic polyether diamine, examples of which will be given below and were m represents the number of monomers of PET, of a molecule containing n monomers of PET, that reacted with the polyether amine. The reaction can be conducted at about 120-140° C. for 24 hours at atmospheric pressure. The value The parameter n can be comprised between about 10 and about 1000. The parameter m can be comprised between 1 and 100.

The above reaction can take place in a batch process.

In other embodiments, the polyethylene terephthalate can be functionalized with polyether amine in a continuous process, in which the polyethylene terephthalate is reacted with polyether amine, with or without grafters or chain extenders, according to the reaction described above, under temperature and pressure conditions suitable to obtain the functionalization reaction in short times, compatible with the residence time of the reagents in a continuously fed volume.

For example, polyester and polyether amine can be fed into an extruder, both in the same position or in different positions along the longitudinal extension of the extruder, i.e. along the extension of the auger or other feeding system of the material along the extruder. For example, polyethylene terephthalate can be fed in an upstream position into a container with longitudinal extension containing a single or double screw feed auger. The polyether amine can be introduced downstream of the feed-in point of the polyethylene terephthalate, with respect to the direction of feed of the auger, in this way coming into contact with polyethylene terephthalate previously melted in a section upstream of the path defined by the feed auger. Downstream of the feed-in point of the polyether amine, this latter reacts with the polyethylene terephthalate thus obtaining the polyester functionalized with polyether amine, which is then extruded in line.

If the reaction takes place with the use of one or more reaction facilitators, for example grafters or chain extenders as described above, these can be introduced together with the polyethylene terephthalate, or subsequently, for example between the feed-in point of the polyethylene terephthalate and the feed-in point of the polyether amine, or together with the polyether amine or downstream of the feed-in point of the polyether amine.

The molten mass of polyethylene terephthalate that has reacted or is reacting with the polyether amine can be extruded to produce threads or filaments, or other semi-finished products of indefinite length.

In some embodiments, with functionalization during extrusion, the polyethylene and the polyether amine can be made to react in the extruder with a residence time of 200-800 seconds, for example comprised between about 300 and about 700 seconds, preferably between about 450 and about 600 seconds, typically about 550 seconds. The residence temperature can be comprised between about 250° C. and about 350° C., preferably between about 270° C. and about 310° C., for example, in particular about 290° C. The pressure in the extruder can be comprised, for instance, between about 100 bar and about 300 bar, preferably between about 100 bar and about 250 bar. The polymeric mass of polyethylene terephthalate functionalized with polyether amine can be extruded with a total flow rate comprised between 10 and 20 kg/h, preferably between 12 and 18 kg/h, for example about 15 kg/h. Exemplary embodiments defined by specific parameters of the monofilament or multifilament thread are described below.

The starting polyethylene terephthalate can have a weighted average molecular weight (Mw) comprised between about 10,000 and about 40,000 and in some embodiments a relative viscosity (method: dichloroacetic acid in 1% solution) that can be comprised between about 0.4 and 1.0 dl/g. In some embodiments the PET can contain percentages by weight of $TiO_2$ up to 2%, preferably up to 1.5%. Examples of polyethylene terephthalate useful for producing modified polyester as described herein, particularly for textile use, are: the polyester RT20 manufactured and marketed by INVISTA Resins & Fibers GmbH & Co KG, Germany; SM-01/D535, marketed by Novapet, Spain.

In other embodiments polyether monoamines, or polyether triamines can be used instead of polyether diamines as indicated by way of example in the previous reactions.

Functionalization processes in which polyethylene terephthalate reacts directly, with or without grafters or chain extenders, with the polyether amine can be of particular interest when the polyester functionalized with polyether amine is intended for the production of continuous threads, for example for textile use. In fact, in this case it is possible to use polyethylene terephthalate in chips and polyether amine as starting materials in an extrusion and spinning process, where the two components (PET and polyether amine) are brought into mutual contact, for example in the extruder, or in a pressurized chamber fluidly coupled with the extruder, at the outlet of which the spinneret is positioned, from which the continuous thread is delivered.

In other embodiments, the modified polymer obtained by reacting PET and polyether amine can be converted once again into chips, granules or into other forms, other than thread, to be used subsequently in any converting process, for example molding, or extrusion.

Some details will be provided below of possible polyether amines that can be used in the production processes of the polyester containing polyethylene terephthalate and polyether amine, using any one of the methods described above.

While in the present description specific reference is made to examples in which a single polyether amine is used, i.e. only one type of polyether amine molecule, it must be understood that in some embodiments more than one polyether amine with different formulas can also be incorporated into the chain of the polyethylene terephthalate.

In some embodiments the polyether amine can be a polyether monoamine with general formula:

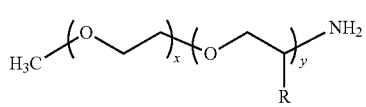

(1)

where R=H for ethylene oxide and R=CH₃ for propylene oxide, and wherein x and y vary according to the number of propylene oxides and ethylene oxides present in the chain. Polyether monoamines of formula (1) are available, for example, from Huntsman Corporation, USA, with the trade name Jeffamine® M series.

In preferred embodiments, the polyether amine has more than one free $NH_2$ group, so that in the reaction with the polyethylene terephthalate one of the $NH_2$ groups forms a covalent bond with the chain of the polyethylene terephthalate while the remaining $NH_2$ groups remain available.

In some embodiments, the polyether amine is a polyether diamine, of formula

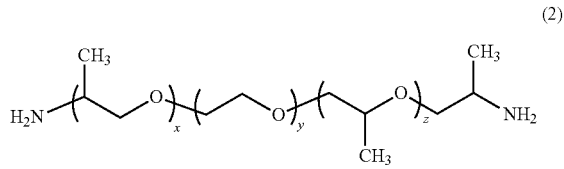

(2)

where x, y and z can vary according to the number of ethylene oxides and propylene oxides present in the chain.

Polyether diamines of general formula (2) are available, for example, from Huntsman Corporation, USA, under the trade name Jeffamine® ED series and Elastamine® RE series.

In preferred embodiments, the polyether diamine has a weighted average molecular weight (Mw) equal to at least about 500 g/mol, preferably equal to at least about 800 g/mol, more preferably equal to at least about 1000 g/mol, even more preferably equal to at least about 1500 g/mol, and preferably no greater than about 5000 g/mol, more preferably no greater than about 3000 g/mol, for example comprised between about 1500 and about 2500 g/mol.

An embodiment provides for the use of Elastamine® RE-2000 (Huntsman) or Jeffamine® ED2003, both of formula (1) wherein:

y is equal to about 39 and (x+z) is equal to about 6, and having a weighted average molecular weight (Mw) of about 2000 g/mol.

In other embodiments polyether diamine of formula (2) with the following characteristics can be used:

y≅12.5; (x+z)≅6, weighted average molecular weight Mw=900 g/mol y≅9; (x+z)≅3.6, weighted average molecular weight Mw=600 g/mol Preferably, the polyether diamine has an AHEW (Amine Hydrogen Equivalent Weight) no greater than 10% with respect to the idealized AHEW. The term (AHEW) is defined as the weighted average molecular weight of the polyether amine divided by the number of active amine hydrogens per molecule. For example, an idealized polyether amine, having a weighted average molecular weight of 2000 g/mol and in which all the ends of the polyether are amine ends, hence contributing with 4 active amine hydrogens per molecule, would have an AHEW of 500 g per equivalent. If 10% of the ends are hydroxyl rather than amine, there will be only 3.6 active amine hydrogens per molecule and the polyether amine will have an AHEW of 556 g per equivalent.

The number of active amine hydrogens per molecule, and hence the AHEW of a given polyether amine, can be calculated according to prior art and conventional techniques, for example by calculating the nitrogen content of the amine groups using the procedure defined by the standard ISO 9702.

In particularly advantageous embodiments, the polyether amine is a polyether diamine, preferably having a weighted average molecular weight equal to or greater than 1500 g/mol and an AHEW that does not exceed by more than 10% the idealized AHEW for this polyether amine.

In embodiments described herein the polyether diamine has a general formula (2) and a composition of the chain with prevalence of PEG (polyethylene glycol) groups with respect to the PPG (polypropylene glycol) groups, i.e. with $y>(x+z)$.

In other embodiments the polyether diamine can have a chain containing polyethylene glycol (PEG) groups and polypropylene glycol (PPG) groups with predominance of PPG groups. Polyether diamines of this type are available from Huntsman Corporation, with the trade name Elastamine® RP series.

In yet other embodiments, the polyether diamine can have a base structure of polypropylene glycol and poly(tetramethylene ether glycol) (PTMEG). Examples of polyether diamines of this type are the polyether diamines marketed by Huntsman Corporation with the trade name Elastamine® RT series.

Although the polyether diamines of the RE series with weighted average molecular weight equal to or greater than about 1500 g/mol and equal to or less than about 2500 g/mol are currently preferred, in particular for applications to polyesters for the production of fibers and threads, it would also be possible to use polyether diamines with a higher weighted average molecular weight, for example up to groups 5000 g/mol, such as Elastamine® RP3-5000 (Huntsman). In other embodiments, the polyether diamine can have weighted average molecular weights (Mw) of less than 1500 g/mol, for example no greater than 1000 g/mol, or no greater than 800 g/mol.

In other embodiments the polyether diamine has a chain composed of polypropylene glycol PPG groups, of general formula

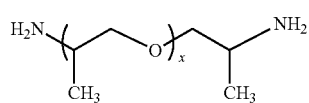

(3)

Examples of polyether diamines of this type are polyether diamines of the Jeffamine® D series produced and marketed by Huntsman Corporation, with weighted average molecular weight (Mw) variable from about 230 g/mol to about 4000 g/mol and in which x can vary from about 2.5 to about 68.

In yet further embodiments, polyether amines with a number of amino groups ($NH_2$) greater than two can be used. For example, the polyether amine can be a polyether triamine of general formula

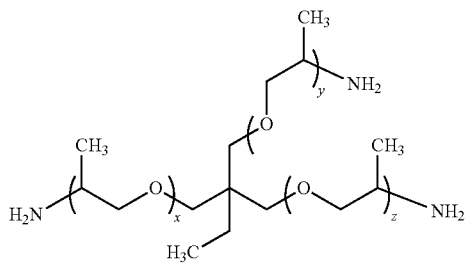

(4.1)

in which $(x+y+z)$ can be comprised between 5 and 6 and the weighted average molecular weight Mw can be equal to about 440 g/mol. In other embodiments the polyether triamine can have the general formula

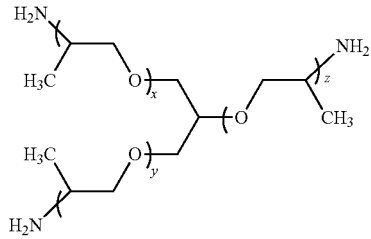

(4.2)

with $x+y+z$ comprised between about 50 and about 85 for average molecular weights (Mw) increasing from about 3000 g/mol to about 5000 g/mol. Polyether triamines of this type are, the Jeffamine® T series produced and marketed by Huntsman Corporation, USA, for instance.

In some embodiments, the amount of polyether amine in the polyester can be comprised between about 1% and about 50% by weight, for example between about 2% and about 30%, preferably between about 2% and about 25% by weight, for example between about 2.5% and about 20% by weight, or between about 5% and about 20% by weight, with respect to the total weight of the polyester.

In some embodiments the polyester comprises an amount of polyethylene terephthalate of at least about 50%, preferably at least about 60%, more preferably at least about 70%, even more preferably at least about 80%, for example at least about 85% by weight with respect to the total weight of the polyester. In embodiments the percentage of polyethylene terephthalate is no greater than about 99%, preferably no greater than about 98%, for example no greater than about 95%, or no greater than about 90%, or than about 85% by weight with respect to the total weight of the polyester.

If the modified polyester containing polyether amine is used in a blend or in combination with other polymers, for example in the case of bi-component fibers, or in the case of blends with fibers, threads or filaments made of other polymers, the percentages of polyethylene terephthalate and of polyether amine indicated above are referred to the total weight of the polyester containing polyethylene terephthalate and polyether amine, excluding the weight of any second or further polymer in the blend.

The polyester usable can have a molar mass for example comprised between about 1,000 and about 1,000,0000 g/mol. In some embodiments, the polyester has a molar mass between about 2,000 and about 1,000,000 g/mol.

The polyester described herein can be advantageously used for producing semi-finished products for the textile industry, in the form of continuous thread or of staple fiber. The thread can be monofilament or multifilament.

The thread can be obtained by extrusion and the staple fiber can be obtained by cutting the extruded continuous thread. The thread obtained from extrusion of the polymer according to the method described herein can be a multifilament textile thread of the LOY (Low Orientation Yarn), POY (Partially Oriented Yarn), or FDY (Fully Drawn Yarn) type.

If the thread is cut into fibers, the fibers can, for example, have a length comprised between about 2 and about 200 mm, preferably between about 10 and about 100 mm. The staple fibers can be converted into continuous yarns using known spinning processes.

According to another aspect, the staple fibers can be used for producing nonwoven fabrics, forming plies of fibers subsequently subjected to mechanical, hydraulic, chemical or thermal bonding processes, or combinations thereof.

The threads or yarns can be used in weaving processes, knitting processes or for other uses.

Threads produced with the process described herein can subsequently be processed to modify their physical and mechanical characteristics. In some embodiments, the threads can be combined with other threads to obtain composite articles. In some embodiments the threads obtained from the spinneret can be texturized, or taslanized, stretched, combined with elastomeric threads for example through an interlacing or covering jet, or other suitable device.

The thread or the fiber can be mono-component. In this case the filament or filaments of which it is formed consist of a single material.

In other embodiments, the thread can be multi-component, for example bi-component. One, some or each filament forming the thread comprises, in this case, two parts formed by two different polymers. In some embodiments the filament comprises an inner core and an outer coating ("core-skin" bi-component fiber) produced in different polymers. According to possible embodiments, the outer part, or skin, that surrounds the inner core can be made of polyester containing polyethylene terephthalate and polyether amine, while the core can be made of a different polymer.

In some embodiments the bi-component fiber can have a second component consisting of or comprising polyamide, polypropylene or thermoplastic polyurethane, or polyester, for example polyethylene terephthalate or polybutylene terephthalate, without polyether amine.

In other embodiments the two components that form each filament can be side by side with one another ("side-by-side" bi-component fiber), rather than inserted one inside the other.

Extrusion heads for producing multi-component, in particular bi-component, threads are known and can be used advantageously in the context of the methods described herein.

In some embodiments, bi-component threads can be produced in which from 10% to 95% by weight, preferably from 50% to 80% by weight, of the polymer of which they are composed is a polyester containing polyethylene terephthalate and polyether amine, while the remaining part consists of polyamide, non-modified polyester, i.e. without polyether amine, or a polymer of another kind, for example polypropylene.

According to the use for which it is destined, the thread can have a number of filaments comprised between 1 (monofilament) and 10,000. In some embodiments the thread can have a count comprised between about 5 and about 6000 dtex, preferably between about 5 and about 5000 dtex, for example between about 5 and about 3000 dtex.

In some embodiments the thread is extruded with a number of filaments comprised between 1 and 300, for example between 5 and 200.

In advantageous embodiments the thread can have a DPF (dtex per filament) value comprised between 0.3 and 20, for example between 0.4 and 20.

In some embodiments, in particular for example for use in the production of garments, the thread can have a number of filaments comprised between 1 (monofilament) and about 100, preferably between about 30 and about 80, in some embodiments between about 40 and about 75, and a count comprised between about 7 and about 140 dtex, preferably between about 40 and about 120 dtex, for example between about 50 and about 100 dtex, in some embodiments about 90 dtex.

In some embodiments the polymer is extruded at an extrusion speed between 20 and 80 cm/s. The filaments exiting from the spinneret can advantageously be cooled in a known manner, for example in a flow of air.

In this step the single filaments are cooled with a lateral flow of air and made to converge toward and through an oiler to be thus combined to form a multifilament thread. Downstream the thread can be fed around one or more stretching and/or relaxing and/or stabilizing rollers, motorized and controlled at peripheral speeds that can differ from one another to give the thread the required and desired degree of stretch and/or orientation.

The thread can be subjected to a stretching and/or texturizing, with elongation percentages comprised between about 15% and about 200%. In some embodiments the thread is subjected to elongation comprised between 20% and 150%.

Finally, the thread is wound to form a reel or package. The winding speed can be comprised between about 1000 and about 5500 m/min, preferably between about 2000 and about 3500 m/min, for example between about 2500 and about 3000 m/min, in some embodiments about 2800 m/min.

Tests on the Antibacterial Properties

Comparative tests on the antibacterial capacity of the polyester containing polyethylene terephthalate and polyether amine were carried out as described below.

The following were produced: samples of fabric knitted on a circular machine with multi-filament thread made of polyethylene terephthalate using chips of polyester RT20 (Invista Resins & Fibers GmbH & Co KG, Germany) with count 50 dtex and 52 filaments, 70 dtex and 60 filaments, 90 dtex and 92 filaments, and samples of fabric knitted on a circular machine with multifilament thread with the same counts and number of filaments indicated above, made of polyester containing polyethylene terephthalate (RT20, Invista) and polyether diamine Elastamine® RE2000 (Huntsman) in an amount of 2.5% by weight on the total weight of the thread. The polyethylene terephthalate functionalized with Elastamine® RE2000 was obtained with a reaction in the extruder, as described above.

The samples of fabric of the two types (with and without polyether amine in the chain of the polyethylene terephthalate) were inoculated with the following microorganisms following the standard ASTM E2315-03:
gram positive bacteria *Staphylococcus aureus* (DSM 346)
gram negative bacteria *Klebsiella pneumoniae* (DSM 789)

FIG. 1 shows the results obtained. The number of microorganisms (in $10^6$) detected for standard polyethylene terephthalate (histogram indicated with PET), and for modified polyethylene terephthalate with the addition of polyether diamine Elastamine® RE2000 (Huntsman) in amount of 2.5% by weight on the total weight of the thread (histogram indicated with Golden Lady PET) is given for each microorganism. As can be seen from FIG. 1, the sample of fabric produced with the modified polyester through functionalization of the polyethylene terephthalate with polyether diamine obtained an antibacterial activity
of 30% with respect to *Staphylococcus aureus*, i.e. a bacterial population growth of 30% lower than that obtained on the reference fabric, produced with the same polyamide, but without polyether amine;
of 18% with respect to *Klebsiella pneumoniae*, i.e. a bacterial population growth of 18% lower than that obtained on the reference fabric, produced with the same polyamide, but without polyether amine.

The indicated data were obtained 24 hours after inoculation of the microorganism and, for each microorganism, two histograms are represented in the histogram: the one on the left relates to the reference sample, made with standard polyethylene terephthalate thread (reference fabric), while the one on the right relates to the sample made with the polyester containing polyethylene terephthalate and polyether diamine.

It is important to note that the international test standards used only establish the procedure to be followed to conduct the test. They do not provide any absolute or even relative comparative criterion to define whether the detected activity is weak, good or excellent. This parameter must be defined on the basis of the final properties of the product (for example odors emitted by the fabric) with which it must ultimately be compared.

Based on the data indicated above, it can be said that the fabrics produced with the use of fibers modified chemically by introduction of polyether amine exhibit a reduction in bacterial growth on the fabric when compared with the same fabrics made with standard fiber. It must be noted that *Klebsiella pneumoniae* is a particularly resistant bacterium and difficult to kill. It is therefore natural that lower values of activity are obtained in relation to it, compared to those obtained in relation to other bacterial strains.

The tests conducted show that the introduction of polyether amine moieties into the chain of the polyethylene terephthalate makes it possible to achieve significant improvements of the polymer, with regard to its antibacterial activity.

EXAMPLES OF PRODUCTION PROCESSES AND OF USE

The examples below illustrate the invention in greater detail.

Example 1—Preparation of Yarns Based on PET with Elastamine RE2000 in Reactive Extrusion The process set forth below describes the preparation of a yarn based on PET (polyethylene terephthalate) functionalized with a polyether diamine called Elastamine RE2000, produced by Huntsman Corporation, USA.

Operating Procedure for Producing the Yarn:

A flow rate of 5 kg/h of PET is fed into an extruder that operates at 290° C., the flow rate of Elastamine RE2000 is 0.26 kg/h and the residence time is 10 minutes (percentage of Elastamine RE2000 equal to 5% by weight over the total weight of polymer).

The following operating procedure for chemical and physical analysis was carried out in order to evaluate the effective functionalization of the yarn obtained with the process now described.

In particular, after washing at 40, 60 and 80° C. in water with a concentration of sodium dodecyl sulfate equal to 5% (weight/volume), conversion of the functionalization reaction equal to 100% was confirmed. Carbon nuclear magnetic resonance also showed the presence of Elastamine RE2000 in the yarn. The typical signals of PET can be noted from the spectrum: δ 167.6 (C=OR), 133.1 (C Ar), 129.3 (C Ar), 63.0 (CH2). The characteristic peak of Elastamine RE2000 is present at 69.15 ppm.

The yarns were then subjected to bacterial culture tests in accordance with ISO 20743 and ASTM 2315-03. Two bacterial strains were used: one Gram positive, *Staphilococcus aureus* (DSM 346) and one Gram negative, *Klebsiella pneumoniae* (DSM 789).

The Tests were Conducted as Follows:

Functionalized PET fabrics were cut into pieces of 0.04 g±0.05 and the numbers used were 6 samples against 6 samples of non-functionalized PET.

The samples were inserted in a multiwell plate and disinfected with an aqueous solution at 70% of ethanol (volume/volume) for 30 min.

The bacterial growth was then evaluated in accordance with ISO 20743 and ASTM 2315-03.

The PET sample functionalized with polyether amine exhibited an ability to allow bacterial growth equal to 5% relativized with respect to the untreated PET sample (100%), both for Gram positive and Gram negative bacteria.

The antifungal activity was evaluated according to the standard ISO 13629-2:2014 using *Aspergillus aculeatus* ATCC 36411 as fungal strain. The sample produced of PET functionalized with polyether amine gave a percentage of fungal growth equal to 2% with respect to that of the untreated PET (100%).

In this and in the subsequent examples, the value of 100% is attributed to the growth of the microorganism in the non-functionalized PET and the bacterial growth capacity in the sample of treated PET is indicated as percentage of that of the untreated PET. Therefore, a percentage of fungal or bacterial growth of 5% means that microorganism growth on the sample tested is equal to 5% of that of the sample of reference, made of untreated PET, i.e. not functionalized with polyether amine.

In modified embodiment, one or more grafters or chain extenders can be added during the reaction step in the extruder.

Example 2—Preparation of Yarns Based on PET with Elastamine RP3-5000 in Reactive Extrusion The process set forth below describes the preparation of a yarn based on PET functionalized with Elastamine RP3-5000 produced by Huntsman Corporation, USA. Elastamine RP3-5000 is a trifunctional primary amine with molecular weight (Mw) equal to about 5000, characterized by oxypropylene repeat units.

Operating Procedure for Producing the Yarn:

A flow rate of 5 kg/h of PET is fed into an extruder that operates at 290° C., the flow rate of RP3-5000 is equal to 0.26 kg/h and the residence time of 10 minutes (percentage of RP3-5000 equal to 5% weight with respect to the total weight of the polymer).

The following operating procedure for chemical and physical analysis was carried out in order to evaluate the effective functionalization of the yarn described in the above process.

In particular, after washing at 40, 60 and 80° C. in water with a concentration of sodium dodecyl sulfate equal to 5% (weight/volume) conversion of the functionalization reaction equal to 98% was confirmed. Carbon nuclear magnetic resonance also showed the presence of RP3-5000 in the yarn. The typical signals of PET can be noted from the spectrum: δ 167.6 (C=OR), 133.1 (C Ar), 129.3 (C Ar), 63.0 (CH2). The characteristic peak of RP3-5000 is present at 69.15 ppm.

The yarns were then subjected to bacterial culture tests in accordance with ISO 20743 and ASTM 2315-03. Two bacterial strains were used: a Gram positive, *Staphilococcus aureus* (DSM 346) and a Gram negative, *Klebsiella pneumoniae* (DSM 789).

The Tests were Conducted as Follows:

PET fabrics functionalized with RP3-5000 were cut into pieces of 0.04 g±0.05 and the numbers used were 6 samples against 6 samples of non-functionalized PET.

The samples were inserted in a multiwell plate and disinfected with an aqueous solution at 70% of ethanol (volume/volume) for 30 min.

The bacterial growth was then evaluated in accordance with ISO 20743 and ASTM 2315-03.

The sample produced with functionalized PET exhibited an ability to allow bacterial growth equal to 40% relativized with respect to the untreated PET sample (100%), both for Gram positive and Gram negative bacteria.

The antifungal activity was evaluated according to the standard ISO 13629-2:2014 using *Aspergillus aculeatus* ATCC 36411 as fungal strain. The sample produced with PET functionalized with polyether amine gave a percentage of fungal growth equal to 1% with respect to that of the untreated PET (100%).

Example 3—Preparation of Yarns Based on PET with Jeffamine M2005 in Reactive Extrusion The process set forth below describes the preparation of a yarn based on PET functionalized with Jeffamine M2005 produced by Huntsman Corporation, USA. Jeffamine M2005 is a monoamine with molecular weight (Mw) of about 2000 g/mol.

Operating Procedure for Producing the Yarn:

A flow rate of 5 kg/h of PET is fed into an extruder that operates at 290° C., the flow rate of Jeffamine M2005 is equal to 0.26 kg/h and the residence time is 10 minutes (percentage of Jeffamine M2005 equal to 5% weight with respect to the total weight of polymer).

The following operating procedure for chemical and physical analysis was carried out in order to evaluate the effective functionalization of the yarn described in the above process.

In particular, after washing at 40, 60 and 80° C. in water with a concentration of sodium dodecyl sulfate equal to 5% (weight/volume), conversion of the functionalization reaction equal to 97% was confirmed. Carbon nuclear magnetic resonance also showed the presence of JA in the yarn. The typical signals of PET can be noted from the spectrum: δ 167.6 (C=OR), 133.1 (C Ar), 129.3 (C Ar), 63.0 (CH2). The characteristic peak of Jeffamine M2005 is present at 69.15 ppm.

The yarns were then subjected to bacterial culture tests in accordance with ISO 20743 and ASTM 2315-03. Two bacterial strains were used: a Gram positive, *Staphilococcus aureus* (DSM 346) and a Gram negative, *Klebsiella pneumoniae* (DSM 789).

The Tests were Conducted as Follows:

PET fabrics functionalized with M2005 were cut into pieces of 0.04 g±0.05 and the numbers used were 6 samples against 6 samples of non-functionalized PET.

The samples were inserted in a multiwell plate and disinfected with an aqueous solution at 70% of ethanol (volume/volume) for 30 min.

The bacterial growth was then evaluated in accordance with ISO 20743 and ASTM 2315-03.

The sample produced with functionalized PET exhibited an ability to allow bacterial growth equal to 55% relativized with respect to the untreated PET sample (100%), both for Gram positive and Gram negative bacteria.

The antifungal activity was evaluated according to the standard ISO 13629-2:2014 using *Aspergillus aculeatus* ATCC 36411 as fungal strain. The sample functionalized with Jeffamine M2005 gave a percentage of fungal growth equal to 1% with respect to that of the untreated PET (100%).

Example 4—Preparation of Yarns Based on PET with Elastamine RE2000

The process set fort below describes the preparation of a yarn based on PET functionalized with Elastamine RE2000 produced by Huntsman Corporation, USA, with direct esterification and subsequent polycondensation.

Operating Procedure for Producing the Yarn:

Ethylene glycol and terephthalic acid are fed into an autoclave equipped with reflux distiller. Operating conditions are pressure between 2.7 and 5.5 bar and temperature between 220 and 260° C. The water coming from polycondensation is removed by distillation.

The esterification steps can also be two and in this case the operating conditions of the second step are 250-270° C. and atmospheric pressure.

The monomer thus obtained is sent to the polymerization reactor that operates at 10-40 mmHg and 250-300° C. with continuous dropwise addition of Elastamine RE2000 for an amount of 5% weight with respect to the total weight of the polymer.

The dry polymer thus obtained is loaded into the extruder to obtain PET yarn functionalized with Elastamine RE2000.

The following operating procedure for chemical and physical analysis was carried out in order to evaluate the effective functionalization of the yarn described in the above process.

In particular, after washing at 40, 60 and 80° C. in water with a concentration of sodium dodecyl sulfate equal to 5% (weight/volume), conversion of the functionalization reaction equal to 100% was confirmed. Carbon nuclear magnetic resonance also showed the presence of JA in the yarn. The typical signals of PET can be noted from the spectrum: δ 167.6 (C=OR), 133.1 (C Ar), 129.3 (C Ar), 63.0 (CH2). The characteristic peak of Elastamine is present at 69.15 ppm.

The yarns were then subjected to bacterial culture tests in accordance with ISO 20743 and ASTM 2315-03. Two bacterial strains were used: a Gram positive, *Staphilococcus aureus* (DSM 346) and a Gram negative, *Klebsiella pneumoniae* (DSM 789).

The Tests were Conducted as Follows.

PET fabrics functionalized with Elastamine RE200 were cut into pieces of 0.04 g±0.05 and the numbers used were 6 samples against 6 samples of non-functionalized PET.

The samples were inserted in a multiwell plate and disinfected with an aqueous solution at 70% of ethanol (volume/volume) for 30 min.

The bacterial growth was then evaluated in accordance with ISO 20743 and ASTM 2315-03.

The sample produced with functionalized PET exhibited an ability to allow bacterial growth equal to 8% relativized with respect to the untreated PET sample (100%), both for Gram positive and Gram negative bacteria.

The antifungal activity was evaluated according to the standard ISO 13629-2:2014 using *Aspergillus aculeatus* ATCC 36411 as fungal strain. The sample produced with functionalized PET gave a percentage of fungal growth equal to 5% with respect to that of the untreated PET (100%).

Example 5—Preparation of Master Batch Based on PET with Elastamine RE2000

The process set forth below describes the preparation of a yarn based on PET functionalized with Elastamine RE2000, Huntsman Corporation, USA, with direct esterification and subsequent polycondensation.

Operating Procedure for Production of the Yarn:

Ethylene glycol and terephthalic acid are fed into an autoclave equipped with reflux distiller. Operating conditions are pressure between 2.7 and 5.5 bar and temperature between 220 and 260° C. The water coming from polycondensation is removed by distillation.

The esterification steps can also be two and in this case the operating conditions of the second step are 250-270° C. and atmospheric pressure.

The monomer thus obtained is sent to the polymerization reactor that operates at 10-40 mmHg and 250-300° C. with continuous dropwise addition of Elastamine RE2000 (30% by weight of Elastamine RE2000 over the total weight).

The dry polymer thus obtained is loaded into the extruder together with commercial (non-functionalized) PET so as to obtain a functionalized PET with Elastamine RE2000 concentration equal to 5% by weight.

The following operating procedure for chemical and physical analysis was carried out, in order to evaluate the effective functionalization of the yarn described in the above process.

In particular, after washing at 40, 60 and 80° C. in water with a concentration of sodium dodecyl sulfate equal to 5% (weight/volume), conversion of the functionalization reaction equal to 100% was confirmed. The typical signals of PET can be noted from the spectrum: $\delta$ 167.6 (C=OR), 133.1 (C Ar), 129.3 (C Ar), 63.0 (CH2). The characteristic peak of Elastamine RE2000 is present at 69.15 ppm.

The yarns were then subjected to bacterial culture tests in accordance with ISO 20743 and ASTM 2315-03. Two bacterial strains were used: a Gram positive, *Staphilococcus aureus* (DSM 346) and a Gram negative, *Klebsiella pneumoniae* (DSM 789).

The tests were Conducted as Follows.

PET fabrics functionalized with Elastamine RE2000 were cut into pieces of 0.04 g±0.05 and the numbers used were 6 samples against 6 samples of nonfunctionalized PET.

The samples were inserted in a multiwell plate and disinfected with an aqueous solution at 70% of ethanol (volume/volume) for 30 min.

The bacterial growth was then evaluated in accordance with ISO 20743 and ASTM 2315-03.

The sample produced exhibited an ability to allow bacterial growth equal to 6% relativized with respect to the untreated PET sample (100%), both for Gram positive and Gram negative bacteria.

The antifungal activity was evaluated according to the standard ISO 13629-2:2014 using *Aspergillus aculeatus* ATCC 36411 as fungal strain. The sample produced gave a percentage of fungal growth equal to 4% with respect to that of the untreated PET (100%).

While in examples 4 and 5 set forth above the master batch of polymer functionalized with polyether amine is obtained in the polymerization reactor, in other possible embodiments preparation of the master batch of PET functionalized with polyether amine can be obtained by means of direct reactive extrusion. In this case, the base polymer, i.e. the commercial PET, is fed together with a polyether amine, which can be selected from those mentioned above, into the extruder. In some embodiments the polyether amine is added in amounts comprised between 10% and 60% preferably between 15% and 50% of the total mass of the polymer. Dosing can take place using volumetric dosers, gravimetric dosers or in combination using both volumetric and gravimetric dosers. The components are fed either in solid (granules or powder) or liquid form. Through the mixing action of the extruder, which can be a two-screw extruder, and the correct residence time, the correct reactivity between PET and polyether amine is obtained. These conditions ensure the necessary cohesion (through the formation of covalent bonds) between the base PET and the polyether amine, to obtain a stable product with permanent properties.

The process can take place in the extrusion step from 250 to 300° C. for a residence time from 60 to 120 seconds as a function of flow rate and type of extruder.

The filament obtained, normally with a diameter in the order of millimeters, is then cooled, for example in water bath at an appropriate temperature, for example typically 30° C. Subsequently the thread is cut into granules or chips. The master batch thus obtained, of PET functionalized with polyether amine, can be used as starting product in the production of a thread or yarn, for example typically multifilament, for textile use.

In this case, the functionalized PET is fed to the extruder in combination with a non-functionalized component, i.e. not containing polyether amine. For example, during extrusion of the final yarn, non functionalized PET is added in an amount such as to obtain, in the final yarn, a content by weight of polyether amine in the order of 5%.

The increase in antibacterial activity deriving from modification of the polyethylene terephthalate through the addition of polyether amine into the polymer chain allows a spinnable polymer material to be obtained, i.e., adapted to give rise to the formation of multifilament or monofilament threads, which can in turn be converted into staple fibers that can be advantageously used to produce textile articles, through conversion of the fiber or of the thread into woven or nonwoven fabrics. These textile articles can be advantageously used in apparel, in particular in sports apparel, due to their capacity to reduce bad smell caused by bacterial growth. In fact, the antibacterial activity, including the antifungal activity, translates into reduced growth of the microorganisms responsible for producing bad smell.

Moreover, the polymer thus modified can also have beneficial applications where a reduction of bacterial load is required, i.e. of the presence of microorganisms, such as bacteria and fungi, also for health and hygiene reasons. Textile materials using modified polyester as described herein, with improved antibacterial properties, can for example be used in the production of gowns, pajamas, sheets, cloths, protective masks, pillowcases, blankets, curtains, bandages, and other articles, all especially for use in hospitals as medical and surgical devices. The polymer can also be used for producing woven and nonwoven fabrics for furnishing articles (upholstery, rugs, carpets), in the domestic and automotive sector, and can advantageously be used to produce filters, in particular air filters, for example for use in air conditioning systems.

The polyester modified with the use of polyether amine in covalent bond with monomers of the polyethylene terephthalate can be used in medical sectors and in surgical procedures, in general in all those uses for which polyethylene terephthalate can currently be used, and in which it may be beneficial to have a polymer with antibacterial properties. For example, the polyether amine can be used to impart antibacterial properties to polyethylene terephthalate destined for the production of threads and membranes for medical use, such as suture threads, membranes for catheter balloons for angioplasty, bandages and medical films, membranes for hemodialysis, materials for the reconstruction of tendons and ligaments, grafts or vascular prostheses, surgical meshes, components of artificial heart valves, etc.

The invention claimed is:

1. A process, comprising:
   providing thread or fiber for producing a textile product with antibacterial properties, said thread or fiber containing a polyester, said polyester containing polyethylene terephthalate modified with an introduction of at least a polyether amine imparting antibacterial properties to said thread or fiber, wherein the polyether amine is prevalently positioned as chain terminal in the polyethylene terephthalate, with an amino terminal ($NH_2$), wherein the polyether amine is present in a percentage between about 5% and about 10% by weight of the total weight of the polyester, wherein the polyether amine has a weighted average molecular weight (Mw) between about 1500 and about 5000.

2. The process of claim 1, wherein the polyether amine is a polyether diamine or a polyether triamine.

3. The process of claim 1, wherein the polyester comprises a percentage of polyethylene terephthalate of between about 50% and about 99% by weight of the total weight of the polyester.

4. The process of claim 1, wherein the polyether amine has a weighted average molecular weight (Mw) between about 1500 g/mol and about 3000 g/mol.

5. A process, comprising:
   forming thread or fiber containing a polyester, said polyester containing polyethylene terephthalate modified with an introduction of at least a polyether amine imparting antibacterial properties to said thread or fiber, wherein the polyether amine is prevalently positioned as chain terminal in the polyethylene terephthalate, with an amino terminal ($NH_2$), wherein the polyether amine is present in a percentage between about 5% and about 10% by weight of the total weight of the polyester, wherein the polyether amine has a weighted average molecular weight (Mw) between about 1500 and about 5000.

6. The process of claim 5, further comprising:
   producing a textile product with antibacterial properties, the textile product comprising the thread or fiber.

7. The process of claim 5, wherein the polyether amine is a polyether diamine or a polyether triamine.

8. The process of claim 5, wherein the polyester comprises a percentage of polyethylene terephthalate of between about 90% and about 95% by weight of the total weight of the polyester.

* * * * *